United States Patent
Li et al.

(10) Patent No.: US 8,288,718 B2
(45) Date of Patent: Oct. 16, 2012

(54) ION MOBILITY SPECTROMETER AND DETECTING METHOD USING THE SAME

(75) Inventors: Yuanjing Li, Beijing (CN); Zhiqiang Chen, Beijing (CN); Qingjun Zhang, Beijing (CN); Shiping Cao, Beijing (CN); Dexu Lin, Beijing (CN); Shaoji Mao, Beijing (CN); Qinghua Wang, Beijing (CN)

(73) Assignee: Nuctech Company Limited, Beijing (CN)

( * ) Notice: Subject to any disclaimer, the term of this patent is extended or adjusted under 35 U.S.C. 154(b) by 124 days.

(21) Appl. No.: 12/997,719

(22) PCT Filed: Jun. 28, 2010

(86) PCT No.: PCT/CN2010/074565
§ 371 (c)(1),
(2), (4) Date: Feb. 17, 2011

(87) PCT Pub. No.: WO2011/000292
PCT Pub. Date: Jan. 6, 2011

(65) Prior Publication Data
US 2011/0133072 A1 Jun. 9, 2011

(30) Foreign Application Priority Data
Jun. 30, 2009 (CN) .......................... 2009 1 0088635

(51) Int. Cl.
*H01J 49/26* (2006.01)
*H01J 49/00* (2006.01)
*B01D 59/44* (2006.01)

(52) U.S. Cl. ........ 250/288; 250/281; 250/282; 250/283; 250/292; 250/287; 250/423 R (58) Field of Classification Search .................. 250/288, 250/281, 282, 283, 292, 287, 423 R
See application file for complete search history.

(56) References Cited

U.S. PATENT DOCUMENTS

| 4,445,038 | A | 4/1984 | Spangler et al. | 250/382 |
|---|---|---|---|---|
| 7,259,369 | B2 | 8/2007 | Scott et al. | 250/287 |
| 7,807,964 | B2 * | 10/2010 | Li et al. | 250/287 |
| 8,013,297 | B2 * | 9/2011 | Peng et al. | 250/296 |
| 8,084,737 | B2 * | 12/2011 | Li et al. | 250/292 |
| 2011/0114837 | A1 * | 5/2011 | Li et al. | 250/286 |

FOREIGN PATENT DOCUMENTS

CN 201141853 10/2008
(Continued)

OTHER PUBLICATIONS

Chinese Office Action (without English translation) for corresponding Chinese Application No. 200910088635.0, dated Jan. 13, 2012, 5 pages.
First Chinese Office Action (without English translation) for corresponding Chinese Application No. 200910088635.0, dated May 10, 2011, 5 pgs.

(Continued)

*Primary Examiner* — Nikita Wells
(74) *Attorney, Agent, or Firm* — Westman, Champlin & Kelly, P.A.

(57) ABSTRACT

An ion mobility spectrometer comprises an electrode and two storage electrodes disposed at the two opposite sides of the electrode respectively. Ions from an intermediate part between the two storage electrodes are stored and the stored ions are released from the storage electrodes by changing electric potentials of the two storage electrodes. The present invention further discloses a detecting method using an ion mobility spectrometer.

21 Claims, 4 Drawing Sheets

FOREIGN PATENT DOCUMENTS

| | | |
|---|---|---|
| CN | 201141853 Y | 10/2008 |
| CN | 101363815 | 2/2009 |
| CN | 201508347 | 6/2010 |
| DE | 11 2009 001 895 T5 | 1/2012 |
| WO | WO2008/042949 | 4/2008 |

OTHER PUBLICATIONS

First German Office Action for German Application No. 11 2010 000 010.7, issued Mar. 21, 2012, 7 pages.

Translation of First German Office Action for German Application No. 11 2010 000 010.7, dated Apr. 11, 2012, 4 pages.

* cited by examiner

ION MOBILITY SPECTROMETER AND DETECTING METHOD USING THE SAME

CROSS-REFERENCE TO RELATED APPLICATION

This Application is a Section 371 National Stage Application of International Application No. PCT/CN2010/074565, filed Jun. 28, 2010, the contents of which are hereby incorporated by reference in their entirety.

BACKGROUND OF THE INVENTION

1. Field of the Invention

The present invention relates to an ion mobility spectrometer and a detecting method using the same.

2. Description of the Related Art

U.S. Pat. No. 7,259,369 B2 disclosed a method of using quadrupole electrical field to hold the positive and the negative ions simultaneously, wherein the positive and the negative ions are located in a storage region. However, there is a need for an improvement in the ion mobility spectrometer.

SUMMARY OF THE INVENTION

In a broad aspect of the present invention there is provided an ion mobility spectrometer, which is capable of detecting positive and negative ions simultaneously.

In accordance with an aspect of the present invention, there is provided an ion mobility spectrometer, comprising: an electrode; two storage electrodes disposed at two opposite sides of the electrode respectively, ions from an intermediate part between the two storage electrodes are stored and the stored ions are released from the storage electrodes by changing electric potentials of the two storage electrodes.

In accordance with another aspect of the present invention, the ion mobility spectrometer further comprises: two leading-out electrodes disposed in a proximity of the two storage electrodes respectively, and located at sides of the two storage electrodes adjacent to the electrode, respectively, the ions from the intermediate part between the two storage electrodes are led to the storage electrodes by means of electric potential differences between the leading-out electrodes and the electrode.

In accordance with another aspect of the present invention, the electrode is a ring-shaped member, and an ionization source is disposed in the ring-shaped member.

In accordance with still another aspect of the present invention, the storage electrodes each have an inner space, and the ions are stored in the inner space.

In accordance with another aspect of the present invention, the leading-out electrodes each have an inner space, and the ions are led to the storage electrodes through the inner spaces of the leading-out electrodes.

In accordance with a further aspect of the present invention, the storage electrodes each comprise a ring-shaped member forming the inner space, and a conductive mesh-like member which is disposed at a side of the ring-shaped member facing away from the intermediate part and is electrically connected with the ring-shaped member.

In accordance with a still further aspect of the present invention, each of the leading-out electrodes is a ring-shaped member forming the inner space.

In accordance with another aspect of the present invention, cross sectional area of the inner space formed by the ring-shaped member of each of the storage electrodes gradually decreases toward the intermediate part.

In accordance with a further aspect of the present invention, the cross sectional area of the inner space formed by the ring-shape member of each of the leading-out electrodes gradually decreases toward the intermediate part.

In accordance with another aspect of the present invention, the inner space formed by the ring-shaped member of each of the storage electrodes substantially has a shape of a truncated cone or a part of a sphere.

In accordance with another aspect of the present invention, the inner space formed by the ring-shaped member of each of the leading-out electrodes substantially has a shape of a truncated cone or a part of a sphere.

In accordance with another aspect of the present invention, the ion mobility spectrometer further comprises: drift region inlet electrodes respectively disposed at sides of the storage electrodes facing away from the leading-out electrodes; each of the drift region inlet electrodes comprises a ring-shaped member forming a cylindrical interior space, and a conductive mesh-like member which is disposed at a side of the ring-shaped member of the drift region inlet electrode adjacent to the storage electrode and is electrically connected with the ring-shaped member of the drift region inlet electrode.

In accordance with another aspect of the present invention, the leading-out electrodes, the storage electrodes, and the electrode are coaxially arranged.

In accordance with another aspect of the present invention, the leading-out electrodes, the storage electrodes, and the electrode and the drift region inlet electrodes are coaxially arranged.

In accordance with another aspect of the present invention, holes of the mesh-like member of the storage electrode are substantially aligned with holes of the mesh-like member of the drift region inlet electrode in an axial direction.

In accordance with another aspect of the present invention, during a storage stage of storing the ions at the storage electrodes, an electric potential of the storage electrode is higher than an electric potential of the drift region inlet electrode and an electric potential of the leading-out electrode for negative ions; and an electric potential of the storage electrode is lower than an electric potential of the drift region inlet electrode and an electric potential of the leading-out electrode for positive ions. During a leading-out stage of leading out the ions from the storage electrodes, the electric potential of the leading-out electrode is lower than the electric potential of the storage electrode and the electric potential of the storage electrode is lower than the electric potential of the drift region inlet electrode for negative ions; and the electric potential of the leading-out electrode is higher than the electric potential of the storage electrode and the electric potential of the storage electrode is higher than the electric potential of the drift region inlet electrode for the positive ions.

In accordance with another aspect of the present invention, the electrode is at an electric potential of zero.

In accordance with a further aspect of the present invention, there is provided a detecting method using an ion mobility spectrometer. The ion mobility spectrometer comprises: an electrode, a first leading-out electrode disposed at a first side of the electrode, a first storage electrode disposed at a side of the first leading-out electrode facing away from the electrode, a first drift region inlet electrode disposed at a side of the first storage electrode facing away from the first leading-out electrode, a second leading-out electrode disposed at a second side of the electrode which is opposite to the first side, a second storage electrode disposed at a side of the second leading-out electrode facing away from the electrode, a second drift region inlet electrode disposed at a side of the second storage electrode facing away from the second leading-out electrode, the method comprises: a step of storing negative ions: storing the negative ions at the first storage electrode by making an electric potential of the first storage electrode higher than an electric potential of the first drift region inlet electrode and an electric potential of the first leading-out electrode; a step of storing positive ions: storing the positive ions at the second storage electrode by making an electric potential of the second storage electrode lower than an electric potential of the second drift region inlet electrode and an electric potential of the second leading-out electrode; wherein the step of storing negative ions and the step of storing positive ions can be carried out simultaneously.

In accordance with a still further aspect of the present invention, the detecting method further comprises: a step of leading out negative ions: leading out the ions from the first storage electrode to a first drift region for detection, by making the electric potential of the first leading-out electrode lower than the electric potential of the first storage electrode, and by making the electric potential of the first storage electrode lower than the electric potential of the first drift region inlet electrode; and a step of leading out positive ions: leading out the ions from the second storage electrode to a second drift region for detection, by making the electric potential of the second leading-out electrode higher than the electric potential of the second storage electrode and by making the electric potential of the second storage electrode higher than the electric potential of the second drift region inlet electrode; wherein the step of leading out negative ions and the step of leading out positive ions can be carried out simultaneously.

Sensitivity and resolution can be effectively improved with simple control through the above configurations and methods.

DETAILED DESCRIPTION OF THE EMBODIMENTS

A further description of the invention will be made as below with reference to embodiments of the invention taken in conjunction with the accompanying drawings.

Figure 1:
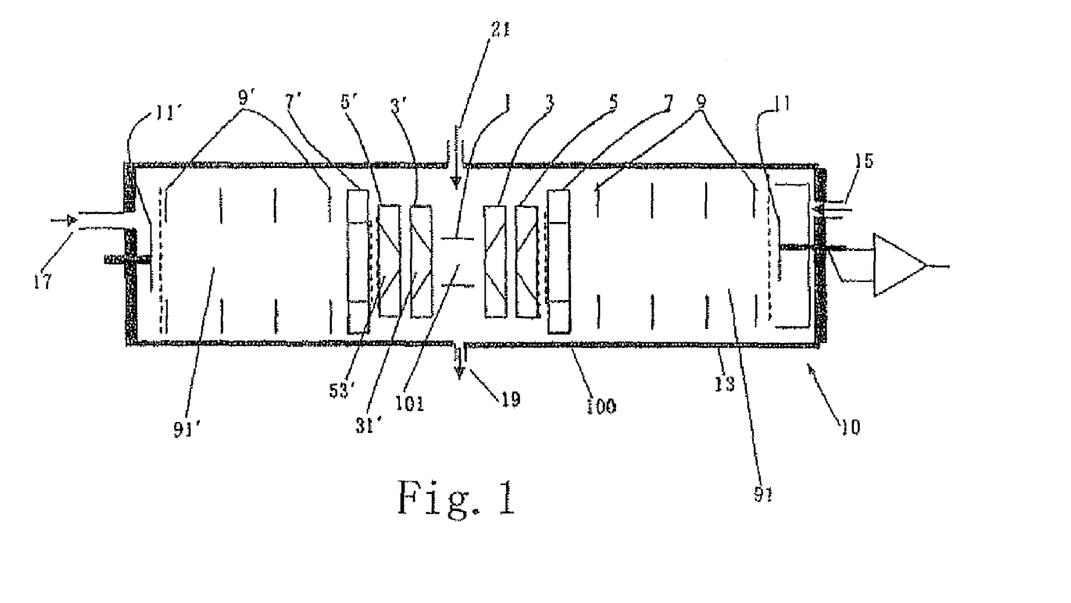
FIG. 1 is a schematic view of an ion mobility spectrometer according to an exemplary embodiment of the present invention.
Figure 2:
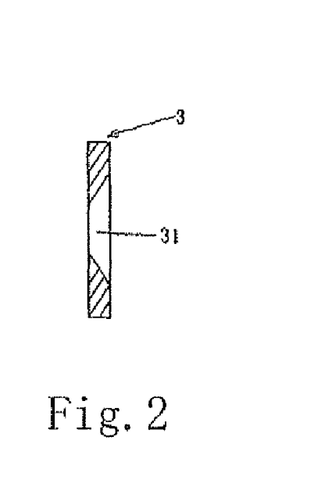
FIG. 2 is a schematic cross sectional view of a leading-out electrode of the ion mobility spectrometer according to an exemplary embodiment of the present invention.
Figure 3:
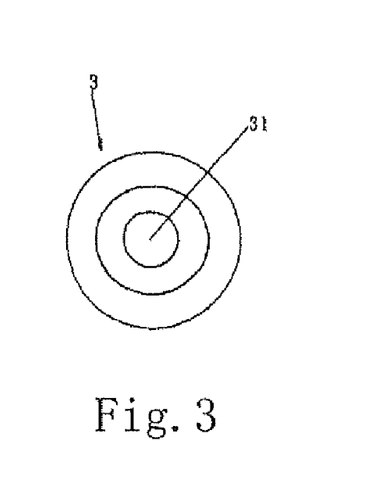
FIG. 3 is a schematic view of the leading-out electrode of the ion mobility spectrometer according to the exemplary embodiment of the present invention.

As illustrated in FIG. 1, an ion mobility spectrometer 10 according to an embodiment of the present invention comprises: an electrode 1 and two storage electrodes 5 and 5' disposed at opposite sides of the electrode 1 respectively. Ions from an intermediate part between the two storage electrodes 5 and 5' (i.e., toward the electrode 1 of FIG. 1) can be stored and the stored ions can be released from the storage electrodes 5 and 5' by changing electric potentials of the two storage electrodes 5 and 5'.

The ion mobility spectrometer 10 according to the embodiment of the present invention may further comprises a housing 100, mobility gas inlets 15 and 17 disposed in the housing 100, a carrier gas and sample inlet 21 and a carrier gas outlet 19. Alternatively, an ionization source 101 may be provided outside the housing 100, and in this case the carrier gas and sample inlet 21 and the carrier gas outlet 19 may be provided in the ionization source 101 correspondingly.

The ion mobility spectrometer 10 may further comprise: two leading-out electrodes 3 and 3', which are disposed at sides of the two storage electrodes 5 and 5' adjacent the electrode 1, and in a proximity of the two storage electrodes 5 and 5', respectively. The ions from the intermediate part between the two storage electrodes 5 and 5' are introduced to the storage electrodes 5 and 5' by means of electric potential difference between the leading-out electrode 3 and 3' and the electrode 1.

The electrode 1 may be a ring-shaped component. The ionization source 101 may be disposed within the ring-shaped component, as illustrated in FIG. 1. The electrode 1 may have any other appropriate shapes, for example, a shape of a disk.

As illustrated in FIGS. 1-4, the leading-out electrodes 3 and 3' have interior spaces 31 and 31' respectively, and ions are introduced to the storage electrodes 5 and 5' through the interior spaces 31 and 31'. Alternatively, in another embodiment of the present invention, the ion mobility spectrometer 10 do not comprise the leading-out electrodes 3 and 3', but the ions are introduced to the storage electrodes 5 and 5' by the electric potential differences between the storage electrodes 5, 5' and the electrode 1. The ions are stored in the storage electrodes 5 and 5' by setting electric potentials of the storage electrodes 5 and 5'.

As shown in FIGS. 1-4, the leading-out electrodes 3 and 3' are ring-shaped components formed with respective interior spaces 31 and 31'. In an embodiment of the present invention, cross sectional areas of the interior spaces 31 and 31' of the leading-out electrodes 3 and 3' gradually decrease toward the intermediate part (i.e., toward the electrode 1 of FIG. 1). Alternatively, the interior spaces 31 and 31' may have other suitable shapes, for example a shape of a cylinder.

As illustrated in FIGS. 1-4, in some embodiments, the interior spaces 31 and 31' of the leading-out electrodes 3 and 3' substantially have a shape of a truncated cone or a partial sphere. The interior spaces 31 and 31' of the leading-out electrodes 3 and 3' may be shaped into other geometrical figurations, for example a space formed by a paraboloid.

Figure 5:
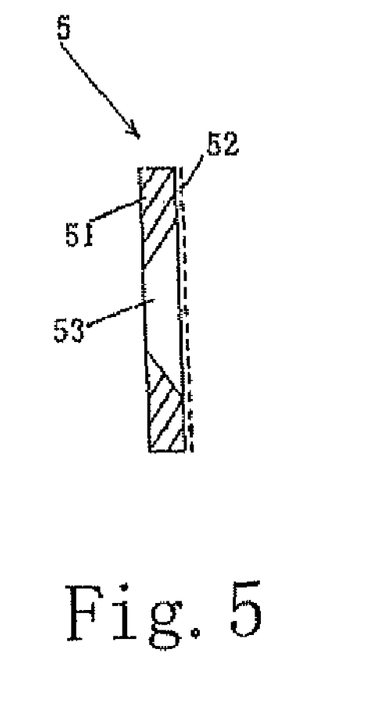
FIG. 5 is a schematic cross sectional view of a storage electrode of an ion mobility spectrometer according to an exemplary embodiment of the present invention.

In an embodiment of the present invention, as shown in FIGS. 1, 5, the storage electrodes 5 and 5' have interior spaces 53 and 53', respectively, and ions are stored in the interior spaces 53 and 53'.

Figure 6:
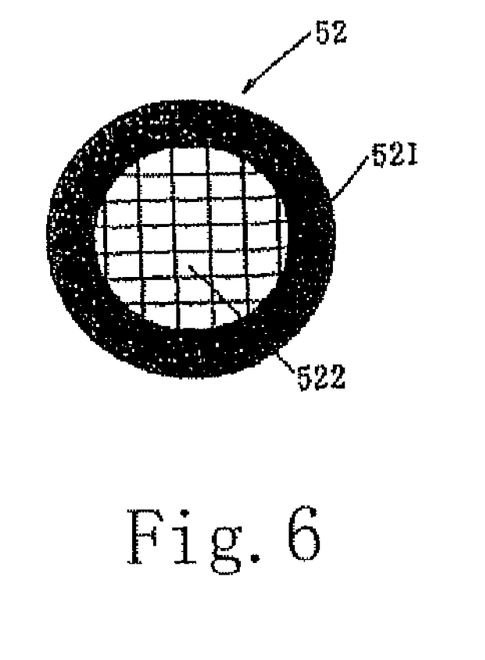
FIG. 6 is a schematic cross sectional view of a conductive mesh-like member of the storage electrode of the ion mobility spectrometer according to the exemplary embodiment of the present invention.

Referring to FIGS. 1, 5, 6, in some embodiments, the storage electrode 5 comprises a ring-shaped member 51 forming the interior space, and a conductive mesh-like member 52 which is disposed at a side of the ring-shaped member 51 facing away from the intermediate part (i.e., facing away from the electrode 1 of FIG. 1) and is electrically connected with the ring-shaped member 51. Similarly, the storage electrode 5' has a same structure as the storage electrode 5. In an embodiment, referring to FIG. 6, the mesh-like member 52 may be composed of a conductive ring-shaped member 521 and a conductive mesh 522 which is electrically and mechanically connected with the ring-shaped member 521. Alternatively, the mesh-like member 52 may be formed by only the conductive mesh. Cross sectional areas of the interior spaces 53 and 53' formed by the ring-shaped members of the storage electrodes 5 and 5' gradually decrease toward the intermediate part (i.e., toward the electrode 1 of FIG. 1). Alternatively, the interior spaces 53 and 53' may have any other appropriate shapes such as a shape of a cylinder. As an example of the storage electrodes 5 and 5', holes of the mesh-like member 52 may comprise various holes such as hexagonal hole, round hole or rectangular hole, etc. The ring-shaped member 51 and the mesh-like member 52 abut against each other and electrically connected with each other. In some embodiments, threads of the mesh-like member 52 are required to be as thin as possible, size of the ion storage regions formed by the storage electrodes is less than 5 mm in an axial direction, and the interior space 53 of the storage electrode forms a region in which an electric field does not exists.

Figure 4:
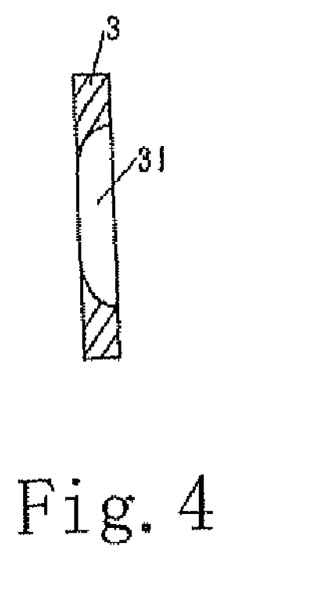
FIG. 4 is a schematic cross sectional view of a leading-out electrode of an ion mobility spectrometer according to another embodiment of the present invention.

Referring to FIGS. 1 and 5, as well as FIG. 4, in some embodiments, the interior spaces 53 and 53' formed by the ring-shaped members of the storage electrodes 5 and 5' may substantially have a shape of a truncated cone or a part of a sphere. It should be appreciated that the interior spaces 53 and 53' formed by the ring-shaped members of the storage electrodes 5 and 5' may be shaped into any other geometrical figurations. For example, the interior spaces 53 and 53' may be a space formed by paraboloid or the like.

Figure 8:
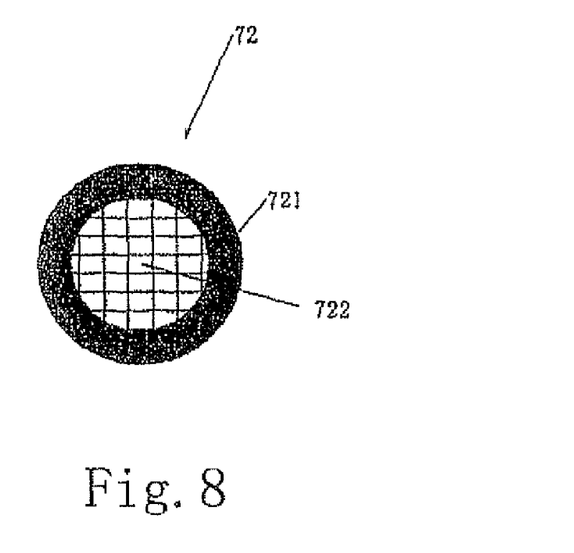
FIG. 8 is a schematic cross sectional view of a conductive mesh-like member of the drift region inlet electrode of the ion mobility spectrometer according to the exemplary embodiment of the present invention.

Referring to FIG. 1 again, the ion mobility spectrometer may further comprise: drift region inlet electrodes 7 and 7' respectively disposed at sides of the storage electrodes 5 and 5' facing away from the leading-out electrodes 3 and 3'. The drift region inlet electrode 7 comprises a ring-shaped member 71 forming a cylindrical interior space 73, and a conductive mesh-like member 72 which is disposed at a side of the ring-shaped member 71 adjacent to the storage electrode 5 and is electrically connected with the ring-shaped member 71 of drift region inlet electrode 7. The drift region inlet electrode 7' has a same structure as the drift region inlet electrode 7. In an embodiment, referring to FIG. 8, the mesh-like member 72 may be composed of a conductive ring-shaped member 721 and a conductive mesh 722 which is electrically and mechanically connected with the ring-shaped member 721. Alternatively, the mesh-like member 72 may be formed by the conductive mesh only.

Figure 7:
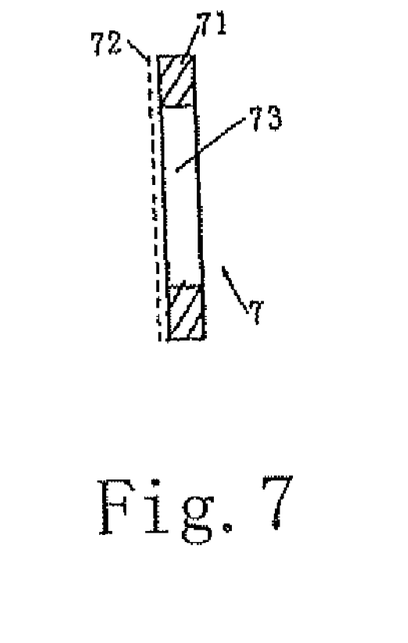
FIG. 7 is a schematic cross sectional view of a drift region inlet electrode of an ion mobility spectrometer according to an exemplary embodiment of the present invention.

Alternatively, the drift region inlet electrodes 7 and 7' may be of other suitable configurations. For example, the drift region inlet electrodes 7 and 7' may have a conical interior space or be merely a ring-shaped member. As an example of the drift region inlet electrode 7, holes of the mesh-like member 72 comprise various holes such as hexagonal holes, round holes, rectangular holes, etc. The ring-shaped member 71 and the mesh-like member 72 abut against each other and are electrically connected with each other.

As illustrated in FIG. 1, in some embodiments, the leading-out electrodes 3 and 3', the storage electrodes 5 and 5', and the electrode 1 are coaxially arranged. In some other embodiments, as shown in FIG. 1, the leading-out electrodes 3 and 3', the storage electrodes 5 and 5', the electrode 1 and the drift region inlet electrode 7 and 7' are in coaxial arrangement.

In some embodiments, as illustrated in FIG. 1, the holes of the mesh-like members of the storage electrodes 5 and 5' are substantially aligned with the holes of the mesh-like members of the drift region inlet electrodes 7 and 7' in the axial direction (i.e. the horizontal direction in FIG. 1). Therefore, probability of annihilation of the ions due to colliding may decrease.

In some embodiments, the ion mobility spectrometer further comprises: the remaining drift region ring electrodes 9 and 9', and Faraday plates 10 and 11, as illustrated in FIG. 1. Furthermore, the above electrodes are separated by insulating material. The ionization source may be an isotope source of 63Ni, usable ionizing technology may include corona discharge, laser, ultraviolet ray, X-rays source and so on. The electrode 1 may serve as a shielding enclosure for the ionization source 101, and may be at a constant zero potential. In some embodiments of the present invention, the ion leading-out electrodes and the storage electrodes may have a shape of a bell mouth.

In some embodiments, a space between the storage electrode 5 and the drift region inlet electrode 7 and a space between the storage electrode 5' and the drift region inlet electrode 7' are less than 3 mm to facilitate entry of the ions into drift regions from the drift region inlet electrodes.

Figure 9:
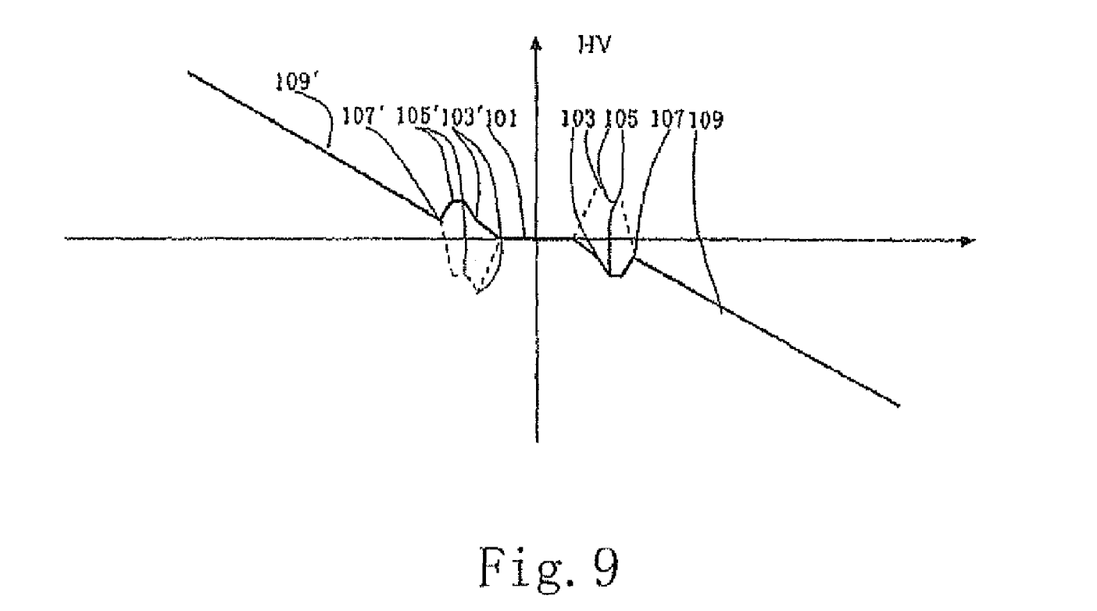
FIG. 9 is a schematic graph of electric potentials of an electrode, leading-out electrodes, storage electrodes, drift region inlet electrodes and remaining drift region electrodes of an ion mobility spectrometer according to an exemplary embodiment of the present invention, wherein the axis of abscissas represents positions of the electrodes and the axis of ordinates represents electric potentials.

As illustrated in FIG. 9, references signs 101, 103, 105, 107, 109, 103', 105', 107', and 109' denote the electric potentials of the electrode 1, the leading-out electrode 3, the storage electrode 5, the drift region inlet electrode 7, the remaining drift region ring electrode 9, the leading-out electrode 3', the storage electrode 5', the drift region inlet electrode 7', the remaining drift region ring electrode 9', respectively. In FIG. 9, the solid lines represent electric potentials in a storage state in which ions are stored in the storage electrodes, and the dashed lines represent electric potentials at which the ions are led from the storage electrodes to the drift regions for detection.

In some embodiments, the electric potentials of the leading-out electrode 3 and the storage electrode 5 may vary.

In some embodiments of the ion mobility spectrometer, during a storage stage of storing the ions at the storage electrodes 5 and 5', the electric potential 105' of the storage electrode 5' is higher than the electric potential 107' of the drift region inlet electrode 7' and the electric potential 103' of the leading-out electrode 3' for negative ions (referring to the left side of FIG. 9), and the electric potential 105 of the storage electrode 5 is lower than the electric potential 107 of the drift region inlet electrode 7 and the electric potential 103 of the leading-out electrode 3 for positive ions (referring to the right side of FIG. 9). During a leading-out stage of leading out the ions from the storage electrodes 5 and 5', the electric potential 103' of the leading-out electrode 3' is lower than the electric potential 105' of the storage electrode 5' and the electric potential 105' of the storage electrode 5' is lower than the electric potential 107' of the drift region inlet electrode 7' for the negative ions; and the electric potential 103' of the leading-out electrode 3' is higher than the electric potential 105' of the storage electrode 5' and the electric potential 105' of the storage electrode 5' is higher than the electric potential 107' of the drift region inlet electrode 7' for the positive ions.

In some embodiments, the electrode 1 is at a potential of zero.

In some embodiments, as illustrated in FIGS. 1 and 9, the electrode 1 serving as the metal shielding enclosure of the ionization source 101, the leading-out electrode 3 and the storage electrode 5 have different electric potentials, a constant electric potential is applied to the drift region inlet electrode 7, and uniformly descending electric potentials are applied to the respective remaining drift region ring electrodes 9 to form the drift region. Therefore, the positive ions are stored, drifted, and collected by the Faraday plate 11. Likewise, the electrode 1, the ion leading-out electrode 3' and the storage electrode 5' have different electric potentials, a constant electric potential is applied to the drift region inlet electrode 7', and uniformly ascending electric potentials are applied to the respective remaining drift region ring electrodes 9' to form the drift region. Therefore, the negative ions are stored, drifted, and collected by the Faraday plate 10. The solid lines 109 and 109' denote the electric potentials of the ring electrodes 9 and 9', respectively. The electric potentials of the ring electrodes 9 and 9' remain stable and constant at the storage stage and the ion leading-out stage.

In some embodiments, at the ion store stage, the positive ions will move to a formed potential trap 105 to be stored, and the negative ions will move to a formed potential trap 105' to be stored. The potential traps with appropriate depth may be formed by adjusting the electric potentials of the electrodes, so as to obtain a maximum storage capability and to push out the ions from the potential traps quickly. The electric potentials of the ion leading-out electrode 3 and the storage electrode 5 are raised simultaneously to levels indicated by the dashed line 103 and 105, and the positive ions are led into the drift region to be drifted and collected. Then, the electric potentials of the ion leading-out electrode 3 and the storage electrode 5 return to the electric potentials applied in the storage state. Likewise, the electric potentials of the ion leading-out electrode 3' and the storage electrode 5' are raised simultaneously to levels indicated by dashed line 103' and 105', and the negative ions are led into the drift region to be drifted and then differentiated. After that the electric potentials of the ion leading-out electrode 3' and the storage electrode 5' return to the electric potentials applied in the storage state.

The present invention further provides a detecting method using the ion mobility spectrometer 10. The ion mobility spectrometer comprises: electrode 1, a leading-out electrode 3' disposed at a side of the electrode 1, a storage electrode 5' disposed at a side of the leading-out electrode 3' facing away from the electrode 1, a drift region inlet electrode 7' disposed at a side of the storage electrode 5' facing away from the leading-out electrode 3', a leading-out electrode 3 disposed at a side of the electrode 1 opposite to the leading-out electrode 3', a storage electrode 5 disposed at a side of the leading-out electrode 3 facing away from the electrode 1, and a drift region inlet electrode 7 disposed at a side of the storage electrode 5 facing away from the leading-out electrode 3. The method comprises: a step of storing negative ions: storing the negative ions at the storage electrode 5' by making an electric potential of the storage electrode 5' higher than electric potentials of the drift region inlet electrode 7' and the leading-out electrode 3'; a step of storing positive ions: storing the positive ions at the storage electrode 5 by making an electric potential of the storage electrode 5 lower than electric potentials of the drift region inlet electrode 7 and the leading-out electrode 3. The step of storing negative ions and the step of storing positive ions can be carried out simultaneously.

In some embodiments, the method further comprises: a step of leading out negative ions: leading out the ions from the storage electrode 5' to a corresponding drift region 91' for detection by making the electric potential of the leading-out electrode 3' lower than the electric potential of the storage electrode 5' and by making the electric potential of the storage electrode 5' lower than the electric potential of the drift region inlet electrode 7'; and a step of leading out positive ions: leading out the ions from the storage electrode 5 to a drift region 91 for detection by making the electric potential of the leading-out electrode 3 higher than the electric potential of the storage electrode 5 and by making the electric potential of the storage electrode 5 higher than the electric potential of the drift region inlet electrode 7. The step of leading out negative ions and the step of leading out positive ions can be carried out simultaneously.

Figure 10:
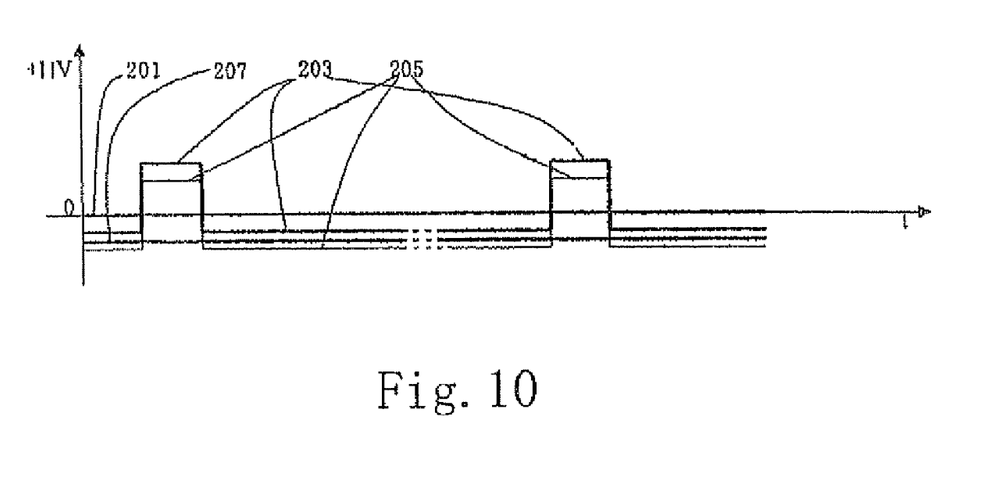
FIG. 10 is a schematic graph showing the electric potentials of the electrode, the leading-out electrode, the storage electrode, the drift region inlet electrode and the remaining drift region electrodes of the ion mobility spectrometer according to an exemplary embodiment of the present invention varying with time, wherein the axis of abscissas represents the time and the axis of ordinates represents the electric potential, and the electric potential of the electrodes is applied for positive ions.

The reference signs 201, 207, 203, and 205 of FIG. 10 are waveforms of the electric potentials of the electrode 1, the drift region inlet electrode 7, the leading-out electrode 3, and the storage electrode 5 varying with time. At the storage stage, the electrode 1 is at the electric potential of zero which is equal to or higher than the electric potential of the leading-out electrode 3. Both of the electric potentials of the leading-out electrode 3 and the drift region inlet electrode 7 are higher than the electric potential of the storage electrode 5. Therefore, the storage region is formed at the storage electrode 5. Meanwhile, the positive ions generated at the ionization source 101 (referring to FIG. 1) are sent to the storage region to be stored. When it is intended to lead out the positive ions from the storage region to the drift region, the electric potentials of the ion leading-out electrode 3 and the storage electrode 5 are raised simultaneously by a magnitude to be higher than the electric potential 207 of the drift region inlet electrode 7. As a result, the positive ions are pushed to the drift region, and then the electric potentials of the ion leading-out electrode 3 and the storage electrode 5 returns to the storage state.

Figure 11:
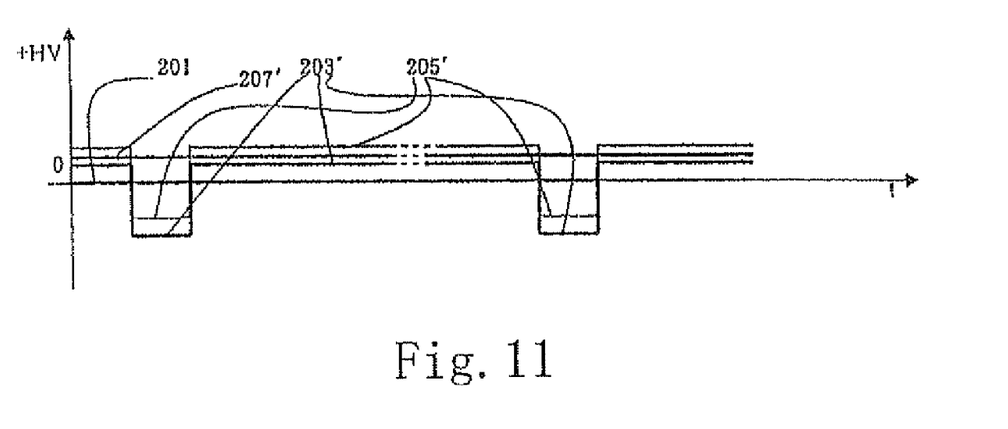
FIG. 11 is a schematic graph showing the electric potentials of the electrode, the leading-out electrode, the storage electrode, the drift region inlet electrode and the remaining drift region electrodes of the ion mobility spectrometer according to an exemplary embodiment of the present invention varying with time, wherein the axis of abscissas represents the time and the axis of ordinates represents the electric potential, and the electric potential of the electrodes are applied for negative ions.

The reference signs 201, 207', 203', and 205' of FIG. 11 are waveforms of the electric potentials of the electrode 1, the drift region inlet electrode 7', the leading-out electrode 3', and the storage electrode 5' varying with time. At the storage stage, the electrode 1 is at the electric potential of zero which is equal to or lower than the electric potential of the leading-out electrode 3'. Both of the electric potentials of the leading-out electrode 3' and the drift region inlet electrode 7' are lower than the electric potential of the storage electrode 5'. Therefore, the storage region is formed at the storage electrode 5'. Meanwhile, the negative ions generated at the ionization source 101 (referring to FIG. 1) are sent to the storage region to be stored. When it is intended to lead out the negative ions from the storage region to the drift region, the electric potentials of the ion leading-out electrode 3' and the storage electrode 5' are lowered simultaneously by a magnitude to be lower than the electric potential 207' of the drift region inlet electrode 7'. As a result, the negative ions are pushed to the drift region, and then the electric potentials of the ion leading-out electrode 3' and the storage electrode 5' returns to the storage state.

As can be seen from the above description, in some embodiments of the present invention, the leading-out electrode provided at the two sides and the electrode provided at the intermediate part form an electric field which facilitates the leading-out of the ions and effectively leads the ions to the storage region. Since the storage electrode may be made to be thin in a direction in which the ions drift, a diameter of the storage electrode may be manufactured to be large, and an intensity of the inner electrical field is almost zero, a large amount of ions can be collected, a thickness of ion cluster is small, and a directional velocity of the ions is almost zero. Hence, a width of the ion mobility spectrum decreases and thus resolution is increased. Besides, the bell-mouth or sphere shaped storage region facilitates leading-out and focusing of the ions. During the ion leading-out stage, by virtue of the bell-mouth shaped leading-out electrode, the effect of a reverse electrical field formed between the ionization source and the leading-out electrode on the leading-out of the ions from the storage electrode is greatly reduced. Because the ions are led to the storage region incessantly at the storage stage, and time for leading the ions out of the storage region is short, sensitivity is greatly enhanced.

The invention claimed is:

1. An ion mobility spectrometer, comprising:
   an electrode;
   two storage electrodes disposed at two opposite sides of the electrode respectively, ions from an intermediate part between the two storage electrodes are stored and the stored ions are released from the storage electrodes by changing electric potentials of the two storage electrodes; wherein the storing of negative ions and of the storing of positive ions can be carried out simultaneously.

2. The ion mobility spectrometer of claim 1, further comprising:
   two leading-out electrodes disposed in a proximity of the two storage electrodes respectively, and located at sides of the two storage electrodes adjacent to the electrode, respectively, the ions from the intermediate part between the two storage electrodes are led to the storage electrodes by means of electric potential differences between the leading-out electrodes and the electrode.

3. The ion mobility spectrometer of claim 2, wherein
   the electrode is a ring-shaped member, an ionization source is disposed in the ring-shaped member.

4. The ion mobility spectrometer of claim 3, wherein
   the storage electrodes each have an inner space, and the ions are stored in the inner space.

5. The ion mobility spectrometer of claim 4, wherein
   the leading-out electrodes each have an inner space, and the ions are led to the storage electrodes through the inner spaces of the leading-out electrodes.

6. The ion mobility spectrometer of claim 5, wherein
   the storage electrodes each comprise a ring-shaped member forming the inner space, and a conductive mesh-like member which is disposed at a side of the ring-shaped member facing away from the intermediate part and is electrically connected with the ring-shaped member.

7. The ion mobility spectrometer of claim 6, wherein
   each of the leading-out electrodes is a ring-shaped member forming the inner space.

8. The ion mobility spectrometer of claim 7, wherein
   cross-sectional area of the inner space formed by the ring-shaped member of each of the storage electrodes gradually decreases toward the intermediate part.

9. The ion mobility spectrometer of claim 8, wherein
   cross-sectional area of the inner space of each of the leading-out electrodes gradually decreases toward the intermediate part.

10. The ion mobility spectrometer of claim 9, wherein
    the inner space formed by the ring-shaped member of each of the storage electrodes substantially has a shape of a truncated cone or a part of a sphere.

11. The ion mobility spectrometer of claim 10, wherein
    the inner space of each of the leading-out electrodes substantially has a shape of a truncated cone or a part of a sphere.

12. The ion mobility spectrometer of claim 11, further comprising:
    drift region inlet electrodes respectively disposed at sides of the storage electrodes facing away from the leading-out electrodes; each of the drift region inlet electrodes comprises a ring-shaped member forming a cylindrical interior space, and a conductive mesh-like member which is disposed at a side of the ring-shaped member of the drift region inlet electrode adjacent to the storage electrode and is electrically connected with the ring-shaped member of the drift region inlet electrode.

13. The ion mobility spectrometer of claim 11, wherein
    the leading-out electrodes, the storage electrodes, and the electrode are coaxially arranged.

14. The ion mobility spectrometer of claim 12, wherein
    the leading-out electrodes, the storage electrodes, and the electrode and the drift region inlet electrodes are coaxially arranged.

15. The ion mobility spectrometer of claim 12, wherein
    holes of the mesh-like member of the storage electrode are substantially aligned with holes of the mesh-like member of the drift region inlet electrode in an axial direction.

16. The ion mobility spectrometer of claim 15, wherein
    during a storage stage of storing the ions at the storage electrodes, an electric potential of the storage electrode is higher than an electric potential of the drift region inlet electrode and an electric potential of the leading-out electrode for negative ions; and an electric potential of the storage electrode is lower than an electric potential of the drift region inlet electrode and an electric potential of the leading-out electrode for positive ions; and
    during a leading-out stage of leading out the ions from the storage electrodes, the electric potential of the leading-out electrode is lower than the electric potential of the storage electrode and the electric potential of the storage electrode is lower than the electric potential of the drift region inlet electrode for the negative ions; and the electric potential of the leading-out electrode is higher than the electric potential of the storage electrode and the electric potential of the storage electrode is higher than the electric potential of the drift region inlet electrode for the positive ions.

17. The ion mobility spectrometer of claim 16, wherein
    the electrode is at an electric potential of zero.

18. A detecting method using an ion mobility spectrometer, the ion mobility spectrometer comprising: an electrode, a first leading-out electrode disposed at a first side of the electrode, a first storage electrode disposed at a side of the first leading-out electrode facing away from the electrode, a first drift region inlet electrode disposed at a side of the first storage electrode facing away from the first leading-out electrode, a second leading-out electrode disposed at a second is side of the electrode which is opposite to the first side, a second storage electrode disposed at a side of the second leading-out electrode facing away from the electrode, a second drift region inlet electrode disposed at a side of the second storage electrode facing away from the second leading-out electrode, the method comprising:

a step of storing negative ions: storing the negative ions at the first storage electrode by making an electric potential of the first storage electrode higher than an electric potential of the first drift region inlet electrode and an electric potential of the first leading-out electrode; and a step of storing positive ions: storing the positive ions at the second storage electrode by making an electric potential of the second storage electrode lower than an electric potential of the second drift region inlet electrode and an electric potential of the second leading-out electrode, wherein the step of storing negative ions and the step of storing positive ions can be carried out simultaneously.

19. The detecting method using the ion mobility spectrometer according to claim 18, further comprising:

a step of leading out negative ions: leading out the ions from the first storage electrode to a first drift region for detection, by making the electric potential of the first leading-out electrode lower than the electric potential of the first storage electrode, and by making the electric potential of the first storage electrode lower than the electric potential of the first drift region inlet electrode; and a step of leading out positive ions: leading out the ions from the second storage electrode to a second drift region for detection, by making the electric potential of the second leading-out electrode higher than the electric potential of the second storage electrode and by making the electric potential of the second storage electrode higher than the electric potential of the second drift region inlet electrode, wherein the step of leading out negative ions and the step of leading out positive ions can be carried out simultaneously.

20. A detecting method using an ion mobility spectrometer, the ion mobility spectrometer comprising: an electrode, a first leading-out electrode disposed at a first side of the electrode, a first storage electrode disposed at a side of the first leading-out electrode facing away from the electrode, a first drift region inlet electrode disposed at a side of the first storage electrode facing away from the first leading-out electrode, a second leading-out electrode disposed at a second side of the electrode which is opposite to the first side, a second storage electrode disposed at a side of the second leading-out electrode facing away from the electrode, and a second drift region inlet electrode disposed at a side of the second storage electrode facing away from the second leading-out electrode, the method comprising:

a step of storing negative ions: forming a storage region at the first storage electrode by making an electric potential of the first leading-out electrode equal to or higher than that of the electrode which is at an electric potential of zero, and making both the electric potential of the first leading-out electrode and an electric potential of the first drift region inlet electrode lower than an electric potential of the first storage electrode; and a step of storing positive ions: forming another storage region at the second storage electrode by making an electric potential of the second leading-out electrode equal to or lower than that of the electrode which is at the electric potential of zero, and making both the electric potential of the second leading-out electrode and an electric potential of the second drift region inlet electrode higher than an electric potential of the second storage electrode, wherein the step of storing negative ions and the step of storing positive ions can be carried out simultaneously.

21. The detecting method using the ion mobility spectrometer according to claim 20, further comprising:

a step of leading out the negative ions: pushing the negative ions to a first drift region for detection, by simultaneously lowering the electric potentials of the first leading-out electrode and the first storage electrode below the electric potential of the first drift region inlet electrode; and a step of leading out the positive ions: pushing the positive ions to a second drift region for detection, by simultaneously raising the electric potentials of the second leading-out electrode and the second storage electrode above the electric potential of the second drift region inlet electrode, wherein the step of leading out the negative ions and the step of leading out the positive ions can be carried out simultaneously.

* * * * *